United States Patent
Fortune et al.

(10) Patent No.: US 7,727,547 B2
(45) Date of Patent: Jun. 1, 2010

(54) TISSUE-ADHESIVE FORMULATIONS

(75) Inventors: David Harry Fortune, Leeds (GB); Graeme Kettlewell, Leeds (GB); David John Mandley, Leeds (GB); Ian Thompson, Leeds (GB); Diane Cook, Leeds (GB)

(73) Assignee: Tissuemed Limited, Leeds (GB)

( * ) Notice: Subject to any disclaimer, the term of this patent is extended or adjusted under 35 U.S.C. 154(b) by 502 days.

(21) Appl. No.: 10/552,095

(22) PCT Filed: Apr. 2, 2004

(86) PCT No.: PCT/GB2004/001464

§ 371 (c)(1),
(2), (4) Date: Oct. 4, 2005

(87) PCT Pub. No.: WO2004/087227

PCT Pub. Date: Oct. 14, 2004

(65) Prior Publication Data

US 2006/0105026 A1    May 18, 2006

(30) Foreign Application Priority Data

Apr. 4, 2000 (GB) .................. 0307765.8
Jul. 25, 2003 (GB) .................. 0317447.1
Aug. 12, 2003 (GB) .................. 0318871.1

(51) Int. Cl.
*A61L 15/00* (2006.01)
*A61K 31/74* (2006.01)

(52) U.S. Cl. .................. 424/445; 424/78.08

(58) Field of Classification Search .................. None
See application file for complete search history.

(56) References Cited

U.S. PATENT DOCUMENTS

| | | |
|---|---|---|
| 4,179,337 A | 12/1979 | Davis et al. |
| 4,453,939 A | 6/1984 | Zimmerman et al. |
| 4,456,711 A | 6/1984 | Pietsch et al. |
| 4,503,034 A | 3/1985 | Maupetit et al. |
| 4,744,364 A | 5/1988 | Kensey |
| 4,804,691 A | 2/1989 | English et al. |
| 4,837,379 A | 6/1989 | Weinberg |
| 4,911,926 A | 3/1990 | Henry et al. |
| 4,913,903 A | 4/1990 | Sudmann et al. |
| 4,940,737 A | 7/1990 | Braatz et al. |
| 5,017,229 A | 5/1991 | Burns et al. |
| 5,066,521 A | 11/1991 | Morsy |
| 5,066,709 A | 11/1991 | Chaudhuri et al. |
| 5,122,614 A | 6/1992 | Zalipsky |
| 5,135,751 A | 8/1992 | Henry et al. |
| 5,162,430 A | 11/1992 | Rhee et al. |
| 5,209,776 A | 5/1993 | Bass et al. |
| 5,292,362 A | 3/1994 | Bass et al. |
| 5,304,595 A | 4/1994 | Rhee et al. |
| 5,306,504 A | 4/1994 | Lorenz |
| 5,312,435 A | 5/1994 | Nash et al. |
| 5,324,775 A | 6/1994 | Rhee et al. |
| 5,328,955 A | 7/1994 | Rhee et al. |
| 5,334,640 A | 8/1994 | Desai et al. |
| 5,410,016 A | 4/1995 | Hubbell et al. |
| 5,462,990 A | 10/1995 | Hubbell et al. |
| 5,468,811 A | 11/1995 | Moro et al. |
| 5,514,379 A | 5/1996 | Weissleder et al. |
| 5,527,856 A | 6/1996 | Rhee et al. |
| 5,571,181 A | 11/1996 | Li |
| 5,575,815 A | 11/1996 | Slepian et al. |
| 5,580,923 A | 12/1996 | Yeung et al. |
| 5,583,114 A | 12/1996 | Barrows et al. |
| 5,614,587 A | 3/1997 | Rhee et al. |
| 5,643,464 A | 7/1997 | Rhee et al. |
| 5,752,974 A | 5/1998 | Rhee et al. |
| 5,770,229 A | 6/1998 | Tanihara et al. |
| 5,786,421 A | 7/1998 | Rhee et al. |
| 5,791,352 A | 8/1998 | Reich et al. |
| 5,874,500 A | 2/1999 | Rhee et al. |
| 5,931,165 A | 8/1999 | Reich et al. |
| 5,989,215 A | 11/1999 | Delmotte et al. |
| 6,007,544 A | 12/1999 | Kim |
| 6,051,648 A | 4/2000 | Rhee et al. |
| 6,063,061 A | 5/2000 | Wallace et al. |
| 6,066,325 A | 5/2000 | Wallace et al. |
| 6,166,130 A | 12/2000 | Rhee et al. |
| 6,264,702 B1 | 7/2001 | Ory et al. |
| 6,312,725 B1 | 11/2001 | Wallace et al. |
| 6,323,278 B2 | 11/2001 | Rhee et al. |
| 6,329,115 B1 * | 12/2001 | Yamashita ............... 430/110.2 |
| 6,379,373 B1 | 4/2002 | Sawhney et al. |
| 6,387,978 B2 | 5/2002 | Ronan et al. |
| 6,391,049 B1 | 5/2002 | McNally et al. |
| 6,458,889 B1 | 10/2002 | Trollsas et al. |
| 6,495,127 B1 | 12/2002 | Wallace et al. |
| 6,548,729 B1 | 4/2003 | Seelich et al. |

(Continued)

FOREIGN PATENT DOCUMENTS

CA    2 363 916 A1    7/2000

(Continued)

OTHER PUBLICATIONS

Machine Translation of DE 3502998 A1.*

(Continued)

*Primary Examiner*—Michael G Hartley
*Assistant Examiner*—Paul Dickinson
(74) *Attorney, Agent, or Firm*—Nixon Peabody LLP (57) ABSTRACT

A tissue-adhesive formulation consists of a naturally occurring or synthetic polymerisable and/or cross-linkable material in particulate form, the polymerisable and/or cross-linkable material being in admixture with particulate material comprising tissue-reactive functional groups. The formulation may be used in the preparation of a tissue-adhesive sheet, by applying the formulation to at least one side of a core of a naturally occurring or synthetic polymeric material.

32 Claims, 3 Drawing Sheets

U.S. PATENT DOCUMENTS

| | | | |
|---|---|---|---|
| 6,566,406 | B1 | 5/2003 | Pathak et al. |
| 6,649,162 | B1 | 11/2003 | Biering et al. |
| 6,664,331 | B2 | 12/2003 | Harris et al. |
| 6,673,093 | B1 | 1/2004 | Sawhney |
| 6,676,962 | B1 | 1/2004 | Müller |
| 6,689,148 | B2 | 2/2004 | Sawhney et al. |
| 6,703,047 | B2 | 3/2004 | Sawhney et al. |
| 6,733,774 | B2 | 5/2004 | Stimmeder |
| 6,800,671 | B1 | 10/2004 | Montgomery et al. |
| 6,818,018 | B1 | 11/2004 | Sawhney |
| 6,833,408 | B2 | 12/2004 | Sehl et al. |
| 6,869,938 | B1 | 3/2005 | Schwartz et al. |
| 6,875,796 | B2 | 4/2005 | Stedronsky |
| 6,887,974 | B2 | 5/2005 | Pathak |
| 6,894,140 | B2 | 5/2005 | Roby |
| 6,916,909 | B1 | 7/2005 | Nicolas et al. |
| 6,921,412 | B1 | 7/2005 | Black et al. |
| 6,923,961 | B2 | 8/2005 | Liu et al. |
| RE38,827 | E | 10/2005 | Barrows et al. |
| 6,989,192 | B2 * | 1/2006 | Husemann et al. .... 428/355 AC |
| 7,009,034 | B2 | 3/2006 | Pathak et al. |
| 7,057,019 | B2 | 6/2006 | Pathak |
| 2002/0013408 | A1 | 1/2002 | Rhee et al. |
| 2002/0042473 | A1 | 4/2002 | Trollsas et al. |
| 2002/0106409 | A1* | 8/2002 | Sawhney et al. ............ 424/484 |
| 2002/0114775 | A1 | 8/2002 | Pathak |
| 2002/0165337 | A1 | 11/2002 | Wallace et al. |
| 2003/0119985 | A1 | 6/2003 | Sehl et al. |
| 2003/0133967 | A1 | 7/2003 | Ruszczak et al. |
| 2004/0102797 | A1 | 5/2004 | Golden et al. |
| 2004/0121951 | A1 | 6/2004 | Rhee |
| 2004/0131554 | A1 | 7/2004 | Rowe et al. |
| 2004/0138329 | A1 | 7/2004 | Hubbell et al. |
| 2004/0191277 | A1 | 9/2004 | Sawhney et al. |
| 2004/0234574 | A9 | 11/2004 | Sawhney et al. |
| 2004/0235708 | A1 | 11/2004 | Rhee et al. |
| 2004/0247691 | A1 | 12/2004 | Marx et al. |
| 2005/0002893 | A1 | 1/2005 | Goldmann |
| 2005/0003012 | A1 | 1/2005 | Woller et al. |
| 2005/0004599 | A1 | 1/2005 | McNally-Heintzelman et al. |
| 2005/0008632 | A1 | 1/2005 | Stimmeder |
| 2005/0010239 | A1 | 1/2005 | Chefitz |
| 2005/0015036 | A1 | 1/2005 | Lutri et al. |
| 2005/0069589 | A1 | 3/2005 | Lowinger et al. |
| 2005/0074495 | A1 | 4/2005 | Schwartz et al. |
| 2005/0085605 | A1 | 4/2005 | Nathan |
| 2005/0096388 | A1 | 5/2005 | Hunter et al. |
| 2005/0107578 | A1 | 5/2005 | Williams et al. |
| 2005/0125012 | A1 | 6/2005 | Houser et al. |
| 2005/0129733 | A1 | 6/2005 | Milbocker et al. |
| 2005/0154125 | A1 | 7/2005 | Rhee |
| 2005/0208095 | A1 | 9/2005 | Hunter et al. |
| 2005/0215748 | A1 | 9/2005 | Milbocker et al. |
| 2005/0228433 | A1 | 10/2005 | Bucay-Couto et al. |
| 2005/0281866 | A1 | 12/2005 | Jarrett et al. |
| 2006/0147409 | A1 | 7/2006 | Pathak et al. |

FOREIGN PATENT DOCUMENTS

| | | | |
|---|---|---|---|
| DE | 3502998 A1 * | 7/1986 | |
| DE | 259 351 A | 8/1988 | |
| DE | 198 59 611 A1 | 6/2000 | |
| EP | 0 099 758 A2 | 2/1984 | |
| EP | 0 226 264 A1 | 6/1987 | |
| EP | 0 732 109 A1 | 9/1996 | |
| EP | 0 846 477 A1 | 6/1998 | |
| EP | 0 930 074 A1 | 7/1999 | |
| EP | 1 003 571 B1 | 5/2000 | |
| EP | 1 216 717 A1 | 6/2002 | |
| EP | 1 216 718 A1 | 6/2002 | |
| WO | WO 92/02238 | 2/1992 | |
| WO | WO 92/14513 | 9/1992 | |
| WO | WO 94/21306 | 9/1994 | |
| WO | WO 96/22054 | 7/1996 | |
| WO | WO 96/22797 | 8/1996 | |
| WO | WO 96/31237 | 10/1996 | |
| WO | WO 97/17025 | 5/1997 | |
| WO | WO 97/22371 | 6/1997 | |
| WO | WO 97/29715 | 8/1997 | |
| WO | 98/16165 A1 | 4/1998 | |
| WO | 1998032474 A1 | 7/1998 | |
| WO | WO 98/48716 | 11/1998 | |
| WO | WO 99/15210 | 4/1999 | |
| WO | WO 99/52481 | 10/1999 | |
| WO | WO 00/02539 | 1/2000 | |
| WO | WO 00/10618 | 3/2000 | |
| WO | 00/38752 A1 | 7/2000 | |
| WO | WO 00/59380 A3 | 10/2000 | |
| WO | WO 01/30405 | 5/2001 | |
| WO | WO 01/30410 | 5/2001 | |
| WO | WO 01/56475 | 8/2001 | |
| WO | WO 01/58452 | 8/2001 | |
| WO | WO 02/09792 A1 | 2/2002 | |
| WO | WO 02/34304 | 5/2002 | |
| WO | WO03094898 A2 * | 5/2002 | |
| WO | WO 02/058749 A2 | 8/2002 | |
| WO | WO 03/020824 A1 | 3/2003 | |
| WO | 2004060405 A2 | 7/2004 | |
| WO | 2004087227 A1 | 10/2004 | |
| WO | 2004108179 A1 | 12/2004 | |
| WO | 2005055958 A2 | 6/2005 | |
| WO | 2005089659 A1 | 9/2005 | |

OTHER PUBLICATIONS

Birch et al., "Methylene Blue Based Protein Solder for Vascular Anastomoses: An In Vitro Burst Pressure Study," *Lasers in Surgery and Medicine* 26:323-329 (2000).

Delgado et al., "The Uses and Properties of PEG-Linked Proteins," *Critical Reviews in Therapeutic Drug Carrier Systems* 9(3,4):249-304 (1992).

Duval et al., "Synthesis and Characterization of Some Covalent Dextran-Polyoxyethyleneglycol Derivatives," *Carbohydrate Polymers* 15:233-242 (1991).

Erout et al., "Radical-Initiated Copolymers of N-vinyl Pyrrolidone and N-Acryloxy Succinimide: Kinetic and Microstructure Studies," *Polymer* 37(7):1157-1165 (1996).

Harris et al., "Synthesis and Characterization of Poly(ethylene Glycol) Derivatives," *J. Polymer Sci.* 22:341-352 (1984).

Mandley et al., "Photon Activated Biological Adhesives in Surgery," *International Journal of Adhesion & Adhesives* 20:97-102 (2000).

Nishi & Kotaka, "Complex-Forming Poly(oxyethylene):Poly(acrylic acid) Interpenetrating Polymer Networks. 1. Preparation, Structure, and Viscoelastic Properties," *Macromolecules* 18(8):1519-1525 (1985).

Sánchez-Chaves et al., "Poly (Vinyl Alcohol) Functionalized by Monosuccinate Groups. Coupling of Bioactive Amino Compounds," *Polymer* 39(13):2751-2757 (1998).

Zalipsky et al., "Attachment of Drugs to Polyethylene Glycols," *Eur. Polym. J.* 19(12):1177-1183 (1983).

Zalipsky et al., "Evaluation of a New Reagent for Covalent Attachment of Polyethylene Glycol to Proteins," *Biotechnology and Applied Biochemistry* 15:100-114 (1992).

Zalipsky et al., "Succinimidyl Carbonates of Polyethylene Glycol: Useful Reactive Polymers for Preparation of Protein Conjugates," *Polymer Reprints*, pp. 173-174 (1990).

Iwata et al., "A Novel Surgical Glue Composed of Gelatin and N-hydroxysuccinimide Activated Poly(L-glutamic acid): Part 1. Synthesis of Activated poly(L-glutamic acid) and its Gelation with Gelatin," *Biomaterials* 19:1869-1876 (1998).

Disley et al., "Covalent Coupling of Immunoglobulin G to a Poly(Vinyl)Alcohol-Poly(Acrylic Acid) Graft Polymer as a Method for Fabricating the Interfacial-Recognition Layer of a Surface Plasmon Resonance Immunosensor," Biosensors and Bioelectronics 13(3-4):383-396 (1998) (abstract only).

Israelachvilli, Jacob, "The Different Faces of Poly(Ethylene Glycol)," Proc. Natl. Acad. Sci. USA 94:8378-8379 (1997).

Don et al., "Studies on the Degradation Behavior of Chitosan-g-Poly (Acylic Acid) Copolymers," Tamkang J. of Science and Engineering 5(4):235-240 (2002).

* cited by examiner

TISSUE-ADHESIVE FORMULATIONS

This is a national stage application under 35 U.S.C. § 371 of PCT/GB2004/001464, filed Apr. 2, 2004, which claims the priority benefit of British patent applications GB 0307765.8 filed Apr. 4, 2003, GB 0317447.1 filed Jul. 25, 2003, and GB 0318871.1 filed Aug. 12, 2003.

FIELD OF THE INVENTION

This invention relates to materials suitable for use as tissue adhesives and sealants, and to a flexible multilamellar sheet, patch or film comprising such materials for topical application to internal and external surfaces of the body, for therapeutic purposes. The invention also relates to a process for the preparation of such products, and to methods of using such products. In particular the invention relates to materials that are formulated as loose or compacted powders and to a self-adhesive, biocompatible and hydratable polymeric sheet with such materials applied to a suitable support, which may be used for therapeutic purposes such as wound healing, joining, sealing and reinforcing weakened tissue, and for drug delivery, and to a process for preparing, and methods of using, such a sheet.

BACKGROUND OF THE INVENTION

There is considerable interest in the use, for a number of surgical or other therapeutic applications, of materials that adhere to biological tissues eg as an alternative to the use of mechanical fasteners such as sutures, staples etc. Formulations of such materials that have hitherto been proposed include viscous solutions or gels that are either manufactured in that form or are prepared immediately prior to use by mixing of the ingredients. Such formulations are then applied to the tissue surface using a suitable applicator device such as a syringe.

Formulations of the type described above suffer from a number of disadvantages. If the formulation is of low viscosity, it may spread from the area of application and hence be difficult to apply precisely to the desired area of tissue. If the formulation is more viscous, on the other hand, it may be difficult to dispense. In either case, the formulation, being prepared in hydrated form, may have a limited lifetime and may be subject to premature curing. It may therefore be necessary for the whole of the formulation to be used at once or discarded. Also, the preparation of formulations immediately prior to use by mixing of ingredients is obviously laborious and time-consuming. In addition to these drawbacks, the degree of adhesion between tissue surfaces that is provided by such formulations may be less than would be desired.

Formulations of tissue adhesive materials have also been applied to a suitable support for application to the tissue surface. The use of therapeutic materials in the form of a sheet, patch or film, for topical administration to either internal or external organs of the body, is well documented for a wide range of medical applications. A disadvantage of products proposed hitherto, however, is that the degree of adhesion to the underlying tissue, particularly in the longer term, may be inadequate. While the initial adhesion may be satisfactory, the sheet may subsequently become detached from the tissue, often after only a few seconds or minutes, eg as a result of hydration of the sheet following its application. In addition, the flexibility of the product may be insufficient for it to conform readily to the surface to which it is applied, which may also have an adverse effect on its adhesion.

As a result of the inadequate adhesion of these products, it may be necessary to provide further reinforcement, eg through mechanical attachment using sutures, staples or the like. Alternatively, energy (eg light or heat energy) may be applied in order to initiate chemical bonding of the adhesive formulation to the underlying tissue, and hence bonding of the tissue surfaces to each other. Clearly, such approaches introduce further drawbacks. The use of mechanical fastenings such as sutures or staples is often the very thing that the use of such products is intended to replace or avoid. In many instances, the use of such fastenings is either not wholly effective (eg on the lung) or undesirable, as their introduction gives rise to further areas of tissue weakness. The use of external energy requires the provision and operation of a source of such energy. Such energy sources may be expensive and difficult to operate, particularly in the confines of an operating theatre or similar environment. Also, the use of external energy for attachment can be both time-consuming and (in some cases) requires significant careful judgement on the part of the surgeon, to evaluate when sufficient energy has been delivered to effect attachment without damaging the underlying tissue.

There have now been devised improved formulations of tissue-adhesive materials and sheets or the like of the general type described above that overcome or substantially mitigate the above-mentioned and/or other disadvantages of the prior art.

BRIEF SUMMARY OF THE INVENTION

According to a first aspect of the invention, there is provided a tissue-adhesive formulation comprising a naturally occurring or synthetic polymerisable and/or cross-linkable material in particulate form, the polymerisable and/or cross-linkable material being in admixture with particulate material comprising tissue-reactive functional groups.

The formulation according to the invention is advantageous primarily in that it can be easily applied to a tissue surface using a simple applicator or delivery device. As it is applied in solid form, the particulate formulation adheres to the tissue surface and does not spread unduly. The formulation exhibits good initial adhesion to the tissue surface, this being believed to be due to van der Waals forces and/or hydrogen bonding between the formulation and the tissue surface. On contact with the tissue surface the formulation becomes hydrated, thereby causing reaction between the tissue-reactive functional groups and the underlying tissue surface. Such reactions between the tissue-reactive functional groups and the underlying tissue results in high adhesion between the formulation and the tissue surface, and hence between tissues hat are joined using the adhesive formulation. Reaction may also take place between the tissue-reactive functional groups and the other components of the formulation to form a strong, flexible and tissue-adherent gel. This formulation thus absorbs physiological fluids (as a consequence of application onto exuding tissue surfaces), and any additional solutions used to hydrate the formulation following application (such fluids can be commonly used solutions used in surgical irrigation), becoming gelatinous and adherent to the tissue surfaces, and thereby providing an adhesive sealant, haemostatic and pneumostatic function.

In addition, because the formulation is made up in solid form that is, until hydrated by contact with the tissue surface (and subsequent hydration), essentially inactive, the formulation is not prone to premature reaction and as a result its shelf-life may be considerable, eg more than six months when stored at room temperature and stored appropriately. This further enables the formulation to be packaged in relatively large quantities that can be dispensed and used over a considerable time period, without the risk of substantial wastage.

According to a second aspect of the present invention, there is provided a sheet having a multilayer structure, said structure comprising a core of a naturally occurring or synthetic polymeric material, the core being coated on at least one side thereof with a tissue-adhesive formulation comprising a naturally occurring or synthetic polymerisable and/or cross-linkable material in particulate form, the polymerisable and/or cross-linkable material being in admixture with particulate material comprising tissue-reactive functional groups.

In preferred embodiments of the invention, the tissue-adhesive formulation is applied to the core by mechanically compressing a blend of material containing tissue-reactive functional groups (hereinafter referred to as "tissue-reactive material") and the polymerisable and/or cross-linkable component, both in particulate form, onto one or both sides of the core.

The sheet according to the invention is advantageous primarily in that it bonds effectively to tissue, enabling it to be used in a variety of medical applications. The invention enables coating of the tissue-reactive materials onto (and into) a three-dimensional structural support, whilst maintaining the pliability and physical properties of the support. Furthermore, the adhesive performance of the tissue-reactive materials is not compromised when delivered to the target tissue in this form. Where, as in preferred embodiments, the support is perforated, the perforations provide a means of anchoring the tissue-reactive materials in the support. This reduces or eliminates cracking and crumbling of the tissue-reactive material as it is applied to the support (core), which would result in sub-optimal coverage of the target tissue, and thereby compromise the adhesive/sealant effects of the sheet.

The sheet exhibits good initial adhesion to the tissue to which it is applied (and may thus be described as "self-adhesive"), and furthermore remains well-adhered to the tissue over a longer timescale. Without wishing to be bound by any theory, it is believed that the initial adhesion of the sheet to the tissue is attributable to electronic bonding of the sheet to the tissue, and this is supplemented or replaced by chemical bonding between the tissue-reactive functional groups of the formulation and the tissue, in particular between amine and/or thiol groups on the tissue surface and the tissue-reactive groups of the sheet. Where the structural inner core of the device is perforated, and is coated on both sides with the tissue-adhesive formulation, the perforations facilitate hydration and cross-linking of the formulation on both sides of the core such that the core becomes enclosed within a three-dimensional matrix of cross-linked material.

The use of the sheet reduces or eliminates the need for additional means of mechanical attachment to the tissue (eg sutures or staples), or the need to provide external energy in the form of heat or light to bring about adherence of the sheet to the underlying tissue. Another advantage of the sheet according to the invention is that it is applied to the tissue as a preformed article, rather than being prepared by mixing of materials immediately prior to use.

By the term "sheet" is meant a three-dimensional article with a thickness that is considerably less than its other dimensions. Such an article may alternatively be described as a patch or a film.

According to another aspect of the invention, there is provided a method for the manufacture of a sheet according to the second aspect of the invention, which method comprises forming a core comprising naturally occurring or synthetic polymeric material, and coating at least one side of said core with a tissue-adhesive formulation comprising a blend of a naturally occurring or synthetic polymerisable and/or cross-linkable material in particulate form and particulate material comprising tissue-reactive functional groups.

In a third aspect, the invention also provides a method of joining a tissue surface to another tissue, or of sealing a tissue surface, which method comprises applying to the tissue surface a formulation according to the first aspect of the invention or a sheet according to the second aspect of the invention.

DETAILED DESCRIPTION OF THE INVENTION

Composition of the Formulation

The formulation according to the first aspect of the invention comprises a naturally occurring or synthetic polymerisable and/or cross-linkable material in particulate form, and a particulate material comprising tissue-reactive functional groups.

These two components may be blended in suitable proportions, which may depend on the particular materials used, as well as the desired properties of the resulting blend. Typically, the ratio by weight of polymerisable and/or cross-linkable material to tissue-reactive material will be between 0.1:1 and 10:1, more preferably between 0.2:1 and 1:1.

The particles that make up the formulation have a wide range of particle sizes. The median particle size may, for instance, lie in the range 5 µm to 500 µm, more preferably 5 µm to 100 µm.

Nature of the Polymerisable and/or Cross-Linkable Component

One component of the formulation is a polymerisable and/or cross-linkable material.

By "polyerisable" is meant that the material may be present in the formulation as a prepolymer or macromer in monomeric or only partially polymerised form, such that upon hydration of the formulation the material undergoes (further) polymerisation.

More commonly, however, the material will be "cross-linkable", rather than "polymerisable". By this is meant that the material will be capable of forming covalent bonds between molecules. Such inter-molecular cross-linking may also be accompanied by intra-molecular cross-linking, ie formation of covalent bonds between functional groups in the same molecule.

The cross-linkable material will generally be polymeric or macromolecular in form, the effect of the cross-linking being to form covalent bonds between such molecules, and so to establish a three-dimensional network or matrix.

The cross-linkable material is preferably selected from polysaccharides, polylactates, polyols and proteins, and derivatives thereof.

The cross-linkable material may be in a partially crosslinked form in which individual molecules of the cross-linkable material are linked together through intermolecular covalent bonds. Such crosslinking can be effected by standard techniques known in the art, for example by heat treatment and/or crosslinking agents. Depending on the nature of the cross-linkable material and/or the conditions employed to effect crosslinking, the degree of crosslinking between individual molecules can vary considerably.

The degree of pre-crosslinking in the cross-linkable material, however, should not be such that it substantially prevents the subsequent reaction of the tissue-reactive functional groups with the cross-linkable material.

Proteins are preferred materials for the cross-linkable material because they are rich in functional groups that are reactive to tissue-reactive functional groups. Hence, the tissue-reactive functional groups will react not only with the tissue surface to which the formulation is applied, but also with the cross-linkable material.

A particularly preferred protein for use in the invention is albumin, particularly mammalian albumin such as porcine, bovine or human albumin.

Preferred synthetic polymers that may be, or may be present in, the polymerisable and/or cross-linkable material include multifunctionally activated synthetic polymers, ie synthetic polymers that have, or have been chemically modified to have, a plurality of functional groups that are capable of reacting with each other or with other functional groups present in the formulation to form covalent bonds. Preferred multifunctionally activated synthetic polymers include chemically modified polyalkylene glycols, in particular polyalkylene glycols that have been modified to contain multiple primary amino or thiol groups.

Suitable modified polyalkylene glycols include both linear and branched (eg so-called "3-arm" and "4-arm") compounds. Examples of suitable multi-amino polymers are those sold under the trade name JEFFAMINE. These are based on backbones of polyethylene glycol and/or polypropylene glycol units with terminal amine groups.

Other suitable synthetic materials may include, or may be based on, poly(vinylamine), poly(ethyleneimine), poly(allylamine), poly(ethylene glycol-co-aspartic acid, poly(lysine-co-lactide, poly(cysteine-co-lactide) or poly(2-aminoethyl-methacrylate).

In general, suitable cross-linkable materials will be materials that are solid at ambient temperatures, and this may preclude the use of very low molecular weight materials.

Methods by which similar and analogous chemically modified polymers can be prepared will be readily apparent to those skilled in the art.

Nature of the Tissue-Reactive Material

The tissue-reactive material is preferably polymeric in nature. Most preferably, the polymer is a synthetic polymer.

By "tissue-reactive functional groups" is meant functional groups capable of reacting with other functional groups present in the tissue surface so as to form covalent bonds between the formulation and the tissue. Tissues generally consist partly of proteins, which commonly contain thiol and primary amine moieties. Many functional groups such as imido ester, p-nitrophenyl carbonate, N-hydroxysuccinimide (NHS) ester, epoxide, isocyanate, acrylate, vinyl sulfone, orthopyridyl-disulfide, maleimide, aldehyde, Iodoacetamide, and others, may react with thiols or primary amines, and therefore constitute "tissue-reactive functional groups". As used herein, the term NHS or NHS ester is intended to encompass not only N-hydroxysuccinimide itself, but also derivatives thereof in which the succinimidyl ring is substituted. An example of such a derivative is N-hydroxysulfosuccinimidyl and salts thereof, particularly the sodium salt, which may increase the solubility of the tissue-reactive material.

Figure 1:
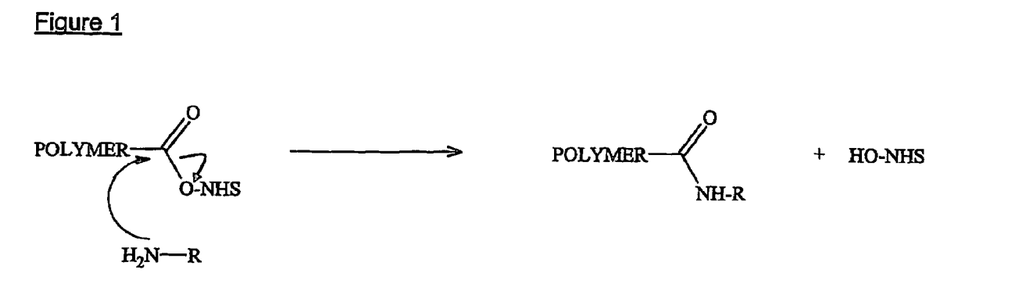
FIG. 1 is a schematic representation of the reaction between a tissue-reactive functional group (in the illustrated case an N-hydroxysuccinimide ester) and an amine-containing molecule such as a tissue protein.

FIG. 1 illustrates the mechanism by which an NHS-functionalised polymer reacts with an amine-containing material such as a tissue protein represented by R—$NH_2$. The reaction is a nucleophilic displacement leading to the formation of an amide bond between the polymer and the tissue protein.

Tissue-reactive functional groups that may be of utility in the present invention are any functional groups capable of reaction (under the conditions prevalent when the formulation is applied to tissue, ie in an aqueous environment and without the application of significant amounts of heat or other external energy) with functional groups present at the surface of the tissue. The latter class of functional group includes thiol and amine groups, and tissue-reactive functional groups therefore include groups reactive to thiol and/or amine groups. Examples are:

imido ester;
p-nitrophenyl carbonate;
N-hydroxysuccinimide (NHS) ester;
epoxide;
isocyanate;
acrylate;
vinyl sulfone;
orthopyridyl-disulfide;
maleimide;
aldehyde; and
iodoacetamide.

N-hydroxysuccinimide (NHS) ester is a particularly preferred tissue-reactive functional group.

In general, the tissue-reactive material may be formed by derivatisation of a suitable polymer precursor. Classes of polymer which lend themselves to such derivatisation include those that contain carboxylic acid or alcohol functional groups, or related structures. Polymers that may be used include polymers that are commercially available or polymers that are prepared specifically for this purpose. Naturally-occurring materials such as sucrose or a derivatised cellulose may also be used.

Figure 2:
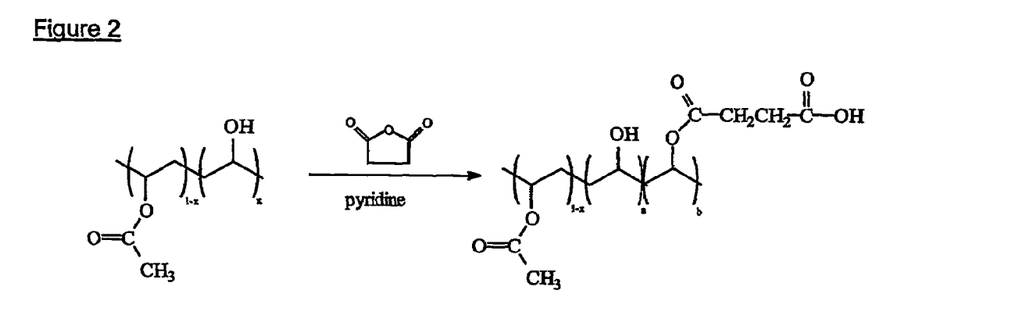
FIG. 2 shows the introduction of carboxyl group-bearing side chains into a poly(vinyl alcohol—vinyl acetate) copolymer.
Figure 3:
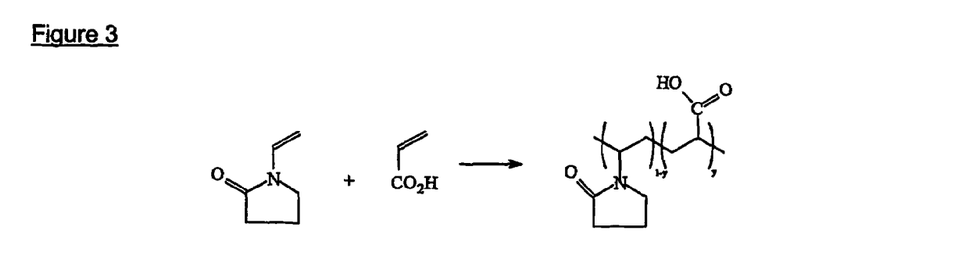
FIG. 3 represents the formation of a poly(N-vinyl-2-pyrrolidone-co-acrylic acid) copolymer.

Commercially available polymers that may be used include polyvinylalcohol (PVA). In the case of PVA, the functional groups may be introduced by first adding a chain extending or linking group, for example an acid functionality that can be further reacted with N-hydroxy succinimide. FIG. 2 shows the addition of a chain-extending group to a copolymer of vinyl acetate and vinyl alcohol, the chain-extending group terminating in a carboxylic acid group that may be converted to the corresponding NHS-ester. The copolymer starting material (in which molar fraction x of vinyl alcohol groups may be 0.85-0.995) is reacted with a cyclic anhydride (in the example illustrated, succinic anhydride) in the presence of a base such as pyridine. Between 5% and 40% of the alcohol groups are derivatised to form the carboxylic acid-bearing side chains (ie a+b=x, with a being between 0.05x and 0.40x), which may then be converted to the NHS-ester by conventional methods that are known per se.

Where the polymer support is synthesized for the purpose of subsequent derivatization, a wide variety of monomers may be used. Examples include N-vinyl-2-pyrrolidone, acrylic acid, vinyl acetate, vinyl acetic acid, mono-2-(methacryloyloxy)ethyl succinate, methacrylic acid, 2-hydroxyethyl methacrylate, 2-hydroxypropyl methacrylate, (polyethylene glycol) methacrylate or other monomers containing acid or alcohol functionality. Such monomers may be polymerised via various standard polymerisation techniques, including free radical techniques using an initiator such as benzoyl peroxide, 2,2'-azobisisobutyronitrile (AIBN), lauroyl peroxide, peracetic acid etc. One preferred example of such a polymer is poly(N-vinyl-2-pyrrolidone-co-acrylic acid) polymerised using AIBN as initiator. The polymerization of this material is illustrated in FIG. 3, in which the molar ratio of acrylic acid-derived units may be between 0 and 1.0, preferably less than 0.60, and more preferably less than 0.40, eg between 0.025 and 0.25. The copolymer may be further reacted with N-hydroxysuccinimide to form the tissue-reactive material.

Preferably, all or substantially all of the available sites in the precursor to the tissue-reactive material will be derivatised (ie the tissue-reactive functional groups will be introduced into all or substantially all of the available sites in the precursor to the tissue-reactive material). The degree of binding between the tissue-reactive functional groups and the tissue to which the formulation is applied will then be a function of the amount of tissue-reactive material in the formulation.

Where, as is preferred, the tissue-reactive functional groups are NHS-esters, at least one of the monomers used in the preparation of the tissue-reactive material must contain a carboxylic acid group or a group capable of being reacted with another material to form an acid functionality.

In the preferred case in which the tissue-reactive material is a derivative of poly(N-vinyl-2-pyrrolidone-co-acrylic acid) copolymer (PVP-co-PAA), the molar ratio of acrylic acid-derived units is preferably between 0.05 and 0.50, and hence that of the vinyl pyrrolidone-derived units is between 0.50 and 0.95. The derivative is referred to as activated PVP-co-PAA.

The acrylic acid groups are preferably derivatised to form tissue-reactive (activated) groups, most preferably with NHS groups. A copolymer of vinyl pyrrolidone and acrylic acid, in which the carboxyl groups of the acrylic acid-derived units carry NHS groups, is referred to herein as NHS-activated PVP-co-PAA.

As noted above, the activity of the tissue-reactive material (ie the degree to which the tissue-reactive functional groups of that material bind to the tissue) may be controlled by varying the proportion of that material in the formulation. The concentration of the tissue-reactive material in the formulation may be varied quite widely, eg from 10% w/w or less up to 50% w/w or more.

The formulation may contain one type of tissue-reactive material, or more than one type of tissue-reactive material.

In addition to forming covalent bonds with the surface to which it is applied, the tissue-reactive material may also have bioadhesive properties. By this is meant that the material should exhibit good initial adhesion to biological tissue to which it is applied. Polymers with such properties typically contain chemical groups with a high ionic density, eg carboxyl, amide, lactam, hydroxyl, ether and ester groups, and the salts thereof, which interact cooperatively with tissue, through the formation of ionic and hydrogen bonds, dipole—dipole interactions and Van der Waals forces. Effective polymers are generally of high molecular weight since the degree of bioadhesion may be proportional to the number of these groups available. Typically, the molecular weight of a bioadhesive polymer will be in excess of about 50,000. The polymers are also generally linear, becoming physically entangled and having an amorphous distribution in solution.

For example, the tissue-reactive polymer may be derivatised PVP or a derivatised copolymer of vinyl pyrrolidone with another monomer (eg acrylic acid). In such a case, the pendant pyrrolidone groups will provide immediate contact adhesion (believed to be due to hydrogen and/or van der Waals bonding, as described above), while the tissue-reactive groups then form covalent bonds with functional groups within the tissue and within the matrix (cross-linking).

Thus, according to another aspect of the invention there is provided a biocompatible and hydratable composition suitable for topical application to internal or external surfaces of the body, which matrix comprises a polymer containing tissue-reactive functional groups and a polymer containing groups that are not tissue-reactive functional groups but which are capable of forming hydrogen bonds with groups at the surface of a tissue to which the matrix is applied.

The tissue-reactive functional groups may be as described above. The groups that are capable of forming hydrogen bonds ("hydrogen-bonding groups") are preferably electron-rich groups, eg selected from amide, lactam, carbonyl, carboxyl, hydroxyl and ether groups.

In a particular embodiment, the tissue-reactive groups and the hydrogen-bonding groups are present in the same polymer. The invention thus provides a biocompatible and hydratable composition suitable for topical application to internal or external surfaces of the body, which composition comprises a polymer containing tissue-reactive functional groups and groups that are not tissue-reactive functional groups but which are capable of forming hydrogen bonds with groups at the surface of a tissue to which the matrix is applied.

The tissue-reactive groups are preferably tissue-reactive ester groups, especially NHS-ester groups, and the hydrogen-bonding groups are preferably amide or lactam groups. The polymer is thus preferably activated PVP-co-PAA, especially NHS-activated PVP-co-PAA.

Alternatively, the tissue-reactive groups and the hydrogen-bonding groups may be present in different polymers. In addition to the tissue-reactive material, therefore, the formulation according to the invention may further comprise a polymer containing hydrogen-bonding groups. Examples of suitable polymers are poly(vinylic acids) and copolymers thereof. However, a preferred group of bioadhesive polymers are polymers consisting of a hydrocarbon backbone with pendant amide or lactam groups, or recurring structural units containing such groups. Preferably, the recurring unit is, or contains, a 1-ethylenepyrrolidin-2-one (vinylpyrrolidone) group. Homopolymers containing recurring N-vinyl-2-pyrrolidone groups are particularly preferred, ie poly(vinylpyrrolidone) (PVP).

PVP has been found to be suitable for use in the present invention for numerous reasons. First, it is readily available in a variety of grades and molecular weights, and has a long history of use in medical applications. PVP has a linear structure, is stable over wide ranges of pH and temperature, and is readily and rapidly soluble in water and other solvents.

Without wishing to be bound by any particular theory, it is believed that the good bioadhesive properties of PVP are attributable to the fact that the carbonyl group and nitrogen atom of the pendant pyrrolidone moiety are electron-rich. The material is therefore capable of effectively immediate adhesion to the tissue to which it is applied through hydrogen bonds formed with functional groups at the surface of the tissue and/or through van der Waals forces.

The bioadhesive polymer may alternatively be a copolymer, eg a copolymer of amide- or lactam-containing units as described above and a vinylic acid. One particular form of copolymer that may be suitable is thus poly(vinylpyrrolidone-co-acrylic acid) (referred to herein as PVP-co-PAA).

Other groups of polymers that may exhibit suitable bioadhesive properties include cellulose derivatives, particularly cellulose ethers and derivatives and salts thereof. Examples include carboxymethyl cellulose (CMC) and salts thereof, hydroxypropylmethyl cellulose and hydroxyethylmethyl cellulose. Sodium carboxymethyl cellulose is one example of such a polymer.

Combinations of polymers of the kinds described above may be employed. One preferred example is a combination of a polymer of amide- or lactam-containing units as described above and a cellulose derivative as described above. A particular combination is PVP and a salt, eg the sodium salt, of CMC.

Sufficiency of the degree of initial adhesion of a sheet to the tissue, by the bioadhesive polymer(s), can be quantitatively determined in vitro, for example by performing an adhesion strength test. This test is performed by allowing the sheet to adhere to a suitable substrate (secured in a fixed position), while the sheet itself is physically attached at a separate point to the load of a tensile testing apparatus, positioned so that, prior to the test, the sheet is not under load. The load cell is moveable along an axis substantially perpendicular to that along which the substrate is positioned. The test involves movement of the load cell away from the substrate, at a constant predetermined rate, until the sheet detaches from the substrate. The output of the test is a quantitative measure of the energy of adhesion for that sheet—ie the cumulative amount of energy required to break the interaction between the sheet and the substrate to which it is adhered. A suitable cumulative energy of adhesion for the sheet according to the invention would be not less than 0.1 mJ, more preferably not less than 0.25 mJ, and most preferably not less than 0.5 mJ.

Manufacture of the Components of the Formulation

The particulate tissue-reactive material and the particulate polymerisable and/or cross-linkable component may be prepared by any suitable means. Particularly where the latter component is proteinaceous, the particles are preferably prepared by freeze- or heat-drying of an aqueous solution or suspension.

To enhance the reaction between the tissue-reactive material (which is typically an electrophile-rich material) and the polymerisable and/or cross-linkable material (which is typically nucleophilic), it may be necessary or desirable to buffer the latter component to alkaline levels to promote proton extraction.

It should be apparent to those skilled in the art that the reaction between electrophilic and nucleophilic compounds may be controlled by adjusting the pH of the reaction. As the pH is adjusted above 7, the crosslinking reaction becomes more favourable.

In preferred embodiments of the present invention, polymerisable and/or cross-linkable nucleophile-rich materials are processed by alkaline buffering and subsequent lyophilisation. These materials are subsequently mixed with tissue-reactive materials in a dehydrated form. Upon hydration (ie during application onto tissue surfaces) the alkaline buffering of the formulation ensures effective reaction between the crosslinkable material and the associated tissue-reactive material.

By using such a method, the need for the components of the formulation to be buffered separately immediately prior to use is eliminated. The novel method described herein eliminates the requirement to "prime" the target site or to prepare a range of buffered solutions in order to effect a cross-linking reaction.

The degree of buffering required is dependent on the cross-linkable material being utilised and the conditions required to abstract a proton therefrom. For example, it has been found that for human albumin the optimal pH required to ensure effective crosslinking is in the range pH 9-11. For synthetic polymeric compounds such as polyvinylamine, on the other hand, equally effective reactivity is demonstrated at pH 7-8.

Thus, in preferred embodiments of the invention, the polymerisable and/or cross-linkable material is buffered to a pH greater than 7.

The formulation may be prepared simply by admixing the components in particulate form, and where desired compacting the formulation to form tablets, plugs or the like. The degree of compaction should be such that the tablets etc retain their integrity until applied to tissue, but not so great as to inhibit hydration (and hence adhesion) after application.

Physical Forms of the Formulation

The formulation according to the invention may have the form of a loose powder, in which particles of the tissue-reactive material are admixed with particles of the polymerisable and/or cross-linkable component.

Alternatively, the formulation may take the form of a compacted body formed by compaction of the particles. Tissue-reactive materials based on poly (N-vinyl-2-pyrrolidone) or copolymers of N-vinyl-2-pyrrolidone with other monomers (eg vinylic monomers) are particularly preferred in such applications, as poly (N-vinyl pyrrolidone) has suitable flow properties for blending with other components of the formulation, and exhibits excellent performance in dry granulation tableting processes as it undergoes plastic deformation on compression, and has low hygroscopicity.

In a further alternative, the formulation may be applied to a core to form a sheet according to the second aspect of the invention.

Sheets in accordance with the invention may be planar, or may be folded, fluted, coiled or otherwise formed into more complex shapes.

The formulation may further comprise additional components such as structural polymers, surfactants, plasticizers and excipients commonly used in tablet manufacture. Such further components may be present as discrete particles, or may be components of the particles of tissue-reactive material and/or polymerisable and/or cross-linkable component.

Nature of the Core

The principal functions of the core are to provide the sheet with structural integrity and to provide a flexible substrate onto which the tissue-reactive formulation, in powder form, can be applied.

The core can be prepared using any suitable polymeric material or combination of materials. The core may be biodegradable or non-biodegradable, and should be biocompatible, ie should be capable of application to tissues either within or external to the body without causing any immunological or other adverse reaction.

Examples of polymeric materials that may be used for the core are:

Polymers or co-polymers based on a-hydroxy acids, such as polylactide, polyglycolide; and also polycaprolactone and other polylactones such as butyro- and valerolactone.

Other examples may include:

alginates (ie polymers based on alginic acid, the polysaccharide obtained from seaweeds);

polyhydroxyalkanoates;

polyamides;
polyethylene;
propylene glycol;
water-soluble glass fibre;
starch;
cellulose;
collagen;
pericardium;
albumin;
polyester;
polyurethane;
polyetheretherketone (PEEK);
polypropylene; and
polytetrafluoroethylene.

The core may be prepared by casting, spinning or foaming of a solution of the polymeric material, or by moulding, weaving of filamentous material, or slicing from a block of material. Appropriate techniques for the preparation of the core by such methods will be familiar to those skilled in the art.

In preferred embodiments, the core is formed with a regular array of apertures, for example in a square or hexagonal array. The apertures may be formed during manufacture of the core or may be introduced after the core is formed, for example by piercing.

Preferably, the apertures are between 50 μm and 2 mm in diameter and adjacent apertures are formed at a centre-to-centre separation of between 100 μm and 5 mm. Preferably, the apertures account for between 5% and 80% of the overall surface area of the core.

The core may have a thickness of from 0.005 to 5 mm.

Application of the Formulation to the Core

The formulation may be applied to just one side of the core. More preferably, however, the formulation is applied to both sides of the core.

Where the core is apertured, application of the formulation to one or both sides of the core causes the apertures to be filled with the formulation. In use, where the formulation is applied to both sides of an apertured core, the formulation that is present in the perforations effectively binds together the activated coatings on each side of the core, encapsulating the core between the two layers of activated coating.

The preferred method for applying the formulation to the core involves mechanically compressing (eg using a hydraulic press) a blend of the tissue reactive material and the polymerisable and/or cross-linkable component, both in particulate form, onto one or both sides of the core.

The blend may be prepared by admixing particles of the tissue-reactive material with particles of the polymerisable and/or cross-linkable component.

The coating formulation may include filler materials that may typically account for up to 50% by weight of the coating formulation. Examples of such materials include cellulose derivatives (eg carboxymethyl cellulose, hydroxypropyl methylcellulose, etc), polyethylene glycol, polyvinylpyrrolidone and other commonly used pharmaceutical excipients.

The thickness of the coating applied to one or both sides of the core will typically be between 50 μm and 500 μm, more commonly from about 70 μm to about 200 μm.

Optionally, a surface of the sheet that, in use, is not intended to adhere to tissue may be coated with a non-adhesive material. Most preferably, such a material is a synthetic polymer. Examples of suitable polymers include polyethylene glycols, polylactide and poly(lactide-co-glycolide). A sheet with such a non-adhesive coating will adhere only to the target tissue (to which the underside of the sheet is applied) and not to surrounding tissues (eg the pleural or peritoneal wall). The non-adhesive coating may include a visibly-absorbing chromophore to enable identification of the non-tissue contacting surface of the sheet. An example of a suitable chromophore is methylthioninium chloride.

The non-adhesive coating is preferably also formed with apertures. In such a case, the apertures may be formed in a similar array to the apertures in the core, with similar separations between apertures. The apertures in the non-adhesive coating are, however, preferably somewhat smaller than those in the core, eg with a diameter of between 50 μm and 1 mm.

Physical Form of the Sheet

The sheet may typically have an overall thickness of from 0.05 to 10 mm, typically 0.05 to 2 mm, and more commonly 0.05 to 0.5 mm, eg about 200 μm or 300 μm or 400 μm.

The sheet may be produced with, or subsequently cut to, dimensions of from a few square millimetres up to several tens of square centimetres.

Therapeutic Applications of the Formulation and Sheet

The formulation and sheet according to the invention are suitable for application to both internal and external surfaces of the body, ie they may be applied topically to the exterior of the body (eg to the skin) or to internal surfaces such as surfaces of internal organs exposed during surgical procedures, including conventional and minimally invasive surgery.

The formulation and sheet according to the invention are particularly suitable for surgical applications in the following areas:
Thoracic/cardiovascular
General surgery
ENT
Urology
Oral/maxillofacial
Orthopaedic
Neurological
Gastroenterology
Ophthalmology
Gynaecology/obstetrics Possible uses are described in more detail below.

Wound Healing

The degradable nature of the formulation and sheet mean that they may support and promote wound healing during both internal and topical procedures. Once the formulation and/or sheet begin to degrade, fibroblasts will move in and begin to deposit components of the extracellular matrix. The formulation and sheet can therefore be used as an internal or external dressing. In addition, factors such as growth factors and cAMP that are known to promote the proliferation of skin cells may be added to the formulation to assist in the healing process. The sheet may be designed to control the transmission of moisture and infectious agents, and thus be useful particularly in the treatment of burns.

Skin Closure

The formulation and sheet may be applied topically to promote wound closure (as an alternative to sutures). This may have beneficial effects in that it may reduce scarring, and the formulation and sheet may thus be useful for cosmetic purposes during minor surgery (eg in Accident and Emergency Departments). The self-adhesive properties of the sheet make it easy to apply quickly.

Hernia Repair

The sheet may be used to provide reinforcement in hernia repair procedures. The self-adhesive attachment overcomes the potential issues faced by conventional surgical reinforcing mesh products, which require suturing or stapling in an already weakened area. The sheet for such a procedure may be engineered to have short or long term durability, depending on the degree of tissue repair required. The sheet may also be able to withstand the application of staples.

Anastomosis

The formulation and self-adhesive sheet provide a means for rapid sealing of, and prevention of leaks in, joined tubular structures such as blood vessels, and vascular and bladder grafts, and the GI tract. The ability of the sheet to support tissue repair may be of particular value if used in nerve repair.

Sealing Large Areas of Tissue

The good sealing and handling properties of the formulation and sheet, combined with their self-adhesive properties and ability to cover a large surface area, mean that they may be of particular use in sealing resected tissue surfaces—in particular those where diffuse bleeding is an issue (eg the liver). The sheet also provides an ideal support matrix for tissue repair at such sites. This could also be applicable to limiting leakage of cerebro-spinal fluid following neurological surgery.

Sealing Air Leaks

In addition to the patch properties described above, the high tensile strength and good inherent elasticity of the formulation and sheet (after hydration and reaction of the tissue-reactive functional groups), make them particularly suitable for sealing air leaks in the lung, particularly following lung resection. Again, after effecting a seal, the sheet provides an ideal support matrix for tissue repair at such sites.

Haemostasis

The formulation and sheet may be applied to a bleeding area, acting as a physical barrier. The tissue-reactive material in the formulation and sheet may immobilise proteins and thereby promote haemostasis.

Therapeutic Agent Administration

Drugs and other therapeutic agents (including biologically active agents such as growth factors, and even cells and cellular components) may be added to solution(s) used to form the components of the formulation and sheet, or covalently linked to components prior to their use in the manufacture of the formulation and sheet. Once the formulation or sheet is in place, following application to the desired site, the drug will be slowly released, either by diffusion or by engineering the formulation or sheet so that as it degrades over time the drug is released. The rate of release can be controlled by appropriate design of the formulation and sheet. The formulation and sheet may thus provide a means for delivering a known amount of drug either systemically or to a precise locus. The drug may be directly bound to a component of the formulation, or simply dispersed in the formulation.

Prevention of Post-Surgical Adhesions

Post-surgical adhesion, the formation of undesired connective tissue between adjacent tissues, is a serious problem which can give rise to major post-surgical complications. It is a particular problem in bowel surgery where it can cause, for instance, twisting of the bowel, which may then necessitate further surgical intervention. The application of sheet material having self-adhesive properties in accordance with the invention to tissues exposed in a surgical procedure can be effective in preventing post-surgical adhesions between that tissue and neighbouring tissues.

Minimally Invasive Procedures

The use of minimally invasive techniques for taking tissue samples by biopsy, inserting devices, delivery of therapeutic agents and performing surgical procedures is rapidly developing as an alternative choice to traditional "open" surgery. Minimally invasive procedures typically result in less pain, scarring, quicker recovery time and fewer post-operative complications for patients, as well as a reduction in health care costs. Procedures are undertaken using specially designed instruments which are inserted through small keyhole-sized surgical incisions. The formulation and sheet may be introduced into the body via existing and specially designed minimally invasive surgery instruments and trocar systems, and the sheet may be shaped or prepared to an appropriate size and configuration. The format of the formulation also may be modified to enable delivery of powders, tablets, pellets, tapes/strips/plegets and other 3-D matrices. The use of a self adhesive formulation will significantly reduce the technical difficulties associated with manipulating, closing and repairing tissues where access is restricted. In addition the sheet properties make them particularly suitable for sealing leaks of air, blood or fluid or for delivery of therapeutic agents.

DETAILED DESCRIPTION OF PREFERRED EMBODIMENTS

The invention will now be described in greater detail, by way of illustration only, with reference to the following Examples.

EXAMPLE 1

Synthesis of NHS-activated PVP-co-PAA (a) Polymerisation of Acrylic Acid and N-vinyl-2-pyrrolidone The polymer is formed via the polymerisation of monomers such as N-vinyl-2-pyrrolidone and acrylic acid, as shown in FIG. 3.

Figure 4:
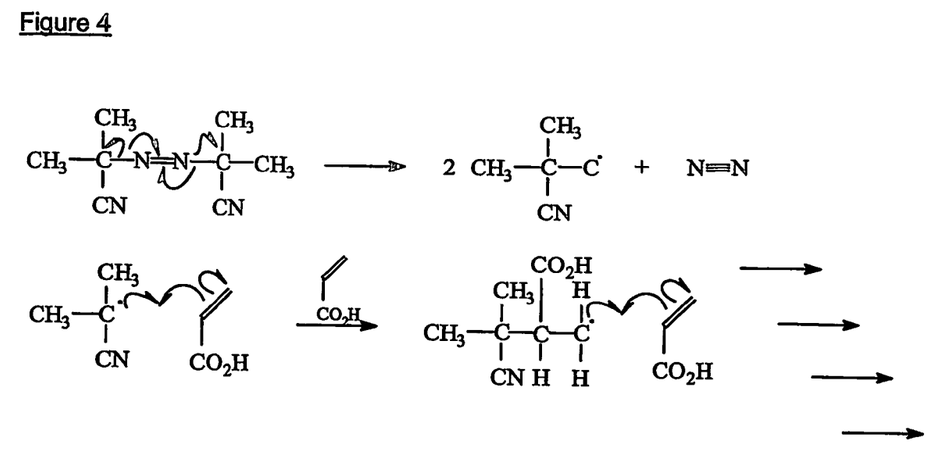
FIG. 4 shows the mechanism of free radical initiation of a polymerisation reaction.

A number of methods may be used to initiate the polymerisation, such as free radical, ionic (cationic or anionic), thermal, UV, redox etc. Free radical polymerisation is the preferred polymerisation method and 2-2'-azo-bis-isobutyrynitrile (AIBN) is the preferred initiator. The AIBN decomposes into two radicals which can then attack the carbon-carbon double bond in the vinylic monomer (acrylic acid) as shown in FIG. 4.

This will continue until termination of chain growth, via combination, disproportionation etc.

The reaction solvent may be N,N'-dimethylformamide, toluene, or any other suitable solvent with a boiling point greater than 100° C. Toluene is the currently preferred solvent.

A typical polymerisation method is as follows:

Solvent is charged to the reaction flask. Usually, around 5-10 ml of solvent per gram of monomer is sufficient. The flask is heated in an oil bath to a temperature sufficient for the generation of free radicals from the chosen initiator. 80-85° C. is the optimum temperature when using AIBN as the initiator. Oxygen-free nitrogen is bubbled through the solvent to remove any dissolved oxygen. Oxygen is also removed from the monomers in the same manner. The initiator is added to the solvent and allowed to dissolve. The monomers are added and the vessel closed. A nitrogen inlet and an escape needle may also be used.

The reaction may be allowed to stand for around 3-24 hours. The reaction mixture is cooled and the polymer is isolated from the solvent/polymer solution by precipitation in 5:1 hexane/isopropanol followed by filtration. Successive washes with diethyl ether are required to remove all traces of polymerisation solvent from the polymer. After successive diethyl ether washes, the polymer is dried under reduced pressure to constant weight.

Typical reaction conditions are shown in Table I:

using a 10-16 μm filter. The polymer is dissolved in 200 ml of N,N-dimethylformamide (DMF) and stirred for approximately 60 minutes before being filtered through a 10-16 μm filter. The polymer is precipitated in approximately 2000 ml of rapidly stirred 5:1 hexane:iso-propanol and isolated by filtration using a 10-16 μm filter. All traces of DMF and toluene are removed by washing and filtration with 500 ml of diethyl ether three times. The polymer is dried for at least 72 hours at 60° C. in vacuo.

TABLE I

| Solvent (vol) | Monomer (g) | | AIBN (g) | T (° C.) | Time (hrs) | Yield | Mw | Mn | Polydispersity Index (Mw/Mn) |
| --- | --- | --- | --- | --- | --- | --- | --- | --- | --- |
| | acrylic acid | N-vinyl-2-pyrrolidone | | | | | | | |
| Toluene (100 ml) | 1.5 (20 mol %) | 8.5 (80 mol %) | 0.02 (0.125%) | 80 | 3 | — | — | — | — |
| Toluene (100 ml) | 0.7 (10 mol %) | 9.3 (90 mol %) | 0.02 (0.125%) | 80 | 3 | 54% | 80040 | 38800 | 2.0 |
| Toluene (100 ml) | 0.7 (10 mol %) | 9.3 (90 mol %) | 0.04 (0.25%) | 80 | 3 | 58% | 74240 | 38340 | 1.9 |
| DMF (100 ml) | 0.7 (10 mol %) | 9.3 (90 mol %) | 0.02 (0.125%) | 80 | 3 | 62% | 54000 | 25150 | 2.1 |
| Toluene (100 ml) | 0.5 (7.5 mol %) | 9.5 (92.5 mol %) | 0.02 (0.125%) | 80 | 3 | — | — | — | — |
| Toluene (100 ml) | 0.35 (5 mol %) | 9.65 (95 mol %) | 0.02 (0.125%) | 80 | 3 | — | — | — | — |

Figure 5:
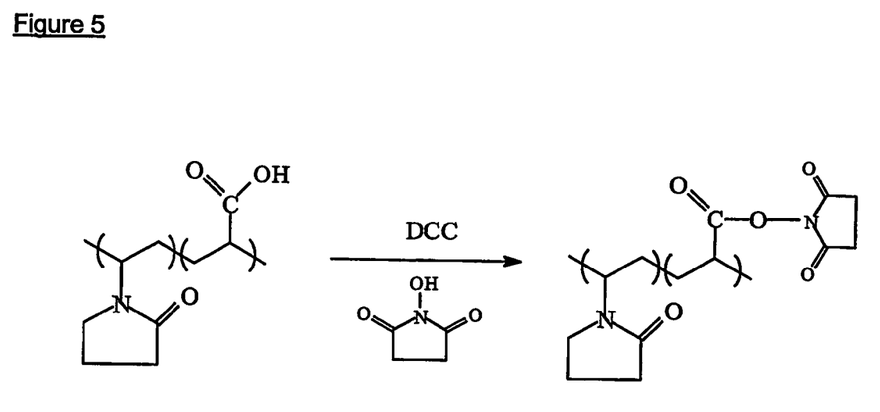
FIG. 5 illustrates the synthesis of a tissue reactive material.

(b) Reaction of PVP-co-PAA and N-hydroxysuccinimide in the Presence of Dicyclohexylcarbodiimide NHS-activated PVP-co-PAA is formed from the reaction of PVP-co-PAA and N-hydroxysuccinimide in the presence of dicyclohexylcarbodiimide (DCC) (FIG. 5).

10 g of PVP-co-PAA containing 0.094 moles of acrylic acid repeat units is dissolved in 50 ml of dried N,N'-dimethylformamide by stirring in a dry 100 ml round bottomed flask. 0.01 moles of N-hydroxysuccinimide (1.15 g) is added to the polymer solution and is allowed to dissolve.

DCC (2.06 g) is melted in an oven at 60° C. and added to the polymer solution. This is left to stir at room temperature for at least 24 hours. The formation of a white precipitate (dicyclohexylurea) is observed. After 24 hours the precipitate is removed by filtration, and the flask and filter washed with a small amount of dry DMF. The polymer is isolated by precipitation in 5:1 hexane/iso-propanol and filtration. The polymer is further purified by repeated washes with dry diethyl ether. The yield is between 50% and 70%.

EXAMPLE 2

Alternative Synthesis of NHS-activated PVP-co-PAA (a) Polymerisation

400ml of dried toluene is heated to 80±2° C. in a round bottomed flask using an oil bath or isomantle. Oxygen is removed from the solvent by bubbling oxygen-free nitrogen through the toluene for at least 30 minutes. 0.1 g (0.006 moles) of azo-iso-butyronitrile (AIBN) dissolved in 2 ml of toluene is added to the reaction flask using a syringe, immediately followed by 45.02 g (0.406 moles) of 1-vinyl-2-pyrrolidone and 7.02 g (0.092 moles) of acrylic acid. The reaction is left under nitrogen at 80±2° C. for 17 hours; the polymer is insoluble in toluene and forms a white precipitate as the reaction proceeds. After 17 hours, a further 0.1 g (0.006 moles) of AIBN is added and the reaction is kept at 80±2° C. for one further hour to polymerise any remaining monomer. The polymer is isolated by pouring into 2000 ml of rapidly stirred 1:1 hexane:diethyl ether and subsequent filtration (b) NHS-esterification.

The acid content of the polymer is calculated by titration against 1.0M NaOH.

20 g of the polymer are dissolved in 160 ml of dry DMF in a 250 ml round-bottomed flask using a magnetic stirrer. 4.28 g (0.037 moles) of NHS are added and allowed to dissolve. 7.67 g (0.037 moles) of dicyclohexyldicarbodiimide are dissolved in 10 ml of dry DMF and added to the polymer/NHS solution. The flask is sealed and the reaction stirred for 96 hours at room temperature. A DMF insoluble material, dicyclohexylurea, is formed as a reaction by product and this is apparent as a white precipitate present in the reaction solution. After 96 hours the dicyclohexylurea is removed by filtration using a 10-16 μm filter and the polymer isolated by precipitation using 1275 ml of 5:1 hexane:iso-propanol. This is removed by filtration using a 10-16 μm filter. The polymer is purified further by dissolving in 170 ml of DMF and precipitation in 1275 ml of 5:1 hexane:iso-propanol three further times. After the final precipitation the polymer is washed by stirring rapidly in 170 ml of diethyl ether until a fine white powder is obtained. This is dried for at least 72 hours at 60° C. in vacuo.

EXAMPLE 3

Blending of NHS-activated PVP-co-PAA with Freeze-Dried Albumin a) Powders of NHS-activated $PVP_{80}$-co-$PAA_{20}$ copolymers (ie copolymers consisting of 80 mol % vinyl pyrrolidone-derived units and 20 mol % acrylic acid-derived units) have been blended (in ratios of 1:1, 2:1 and 4:1) with freeze-dried porcine albumin (Sigma Aldrich; previously buffered to pH 10.5).

b) Powders of NHS-activated $PVP_{70}$-co-$PAA_{30}$ copolymers (70 mol % vinyl pyrrolidone: 30mol % acrylic acid) have been blended (1:1) with freeze-dried human albumin (Baxter human albumin solution (20%) previously buffered to pH 10.5).

c) Powders of NHS-activated $PVP_{70}co\text{-}PAA_{30}$ copolymers have been blended (2:1) with freeze-dried porcine albumin (previously buffered to pH 10.5).

EXAMPLE 4

Blending of NHS-activated PVP-co-PAA with Freeze-Dried Albumin and Application to Liver Tissue a) Powders of NHS-activated $PVP_{80}\text{-}co\text{-}PAA_{20}$ have been blended (1:1) with freeze-dried porcine albumin (Sigma Aldrich; previously buffered to pH 10.5) and delivered onto moist liver tissue. The powder rehydrated rapidly (<5 minutes) yielding a gel that offers cohesive strength, in addition to exhibiting strong adhesion to the underlying tissue surface.

b) Powders of NHS-activated $PVP_{70}\text{-}co\text{-}PAA_{30}$ have been blended (1:1) with freeze-dried human albumin (Baxter human albumin solution (20%) previously buffered to pH 10.5) and delivered onto moist liver tissue. The powder rehydrated rapidly (<5 minutes) yielding a gel that offers cohesive strength, in addition to exhibiting strong adhesion to the underlying tissue surface.

EXAMPLE 5

Blending of NHS-activated PVP-co-PAA with Freeze-Dried Porcine Albumin, Forming a Compressed Disc Followed by Application to Liver Tissue Powders of NHS-activated $PVP_{70}\text{-}co\text{-}PAA_{30}$ copolymers have been blended (2:1) with freeze dried porcine albumin (previously buffered to pH 10.5), followed by compression into a thin (<2 mm thick) disc and delivered onto moist liver tissue. The disc adheres immediately to the liver tissue and rehydrates gradually over an hour yielding a gel that offers cohesive strength, in addition to exhibiting strong adhesion to the underlying tissue surface.

EXAMPLE 6

Blending of Excipients with Powdered NHS-activated $PVP_{80}\text{-}co\text{-}PAA_{20}$ and Freeze-Dried Porcine Albumin Previously Buffered to pH 10.5 (PSA)

Powders of NHS-activated $PVP_{80}co\text{-}PAA_{20}$ and PSA (1:1) have been blended with excipients such as hydroxypropyl cellulose, poly(vinyl pyrrolidone) and microcrystaline cellulose. The powdered mixture was compressed into a disc with a thickness of less than 2 mm. These discs adhered immediately to moist porcine liver tissue and rehydrated upon immersion in aqueous solution. After immersion in aqueous solution for 1 hour, they remained adhered to tissue as a crosslinked gel. Adhesion was obtained with concentrations of NHS-activated $PVP_{80}\text{-}co\text{-}PAA_{20}$ and PSA from 11.5% to 50% w/w.

EXAMPLE 7

Schematic Representation of a Sheet According to the Invention

Figure 6:
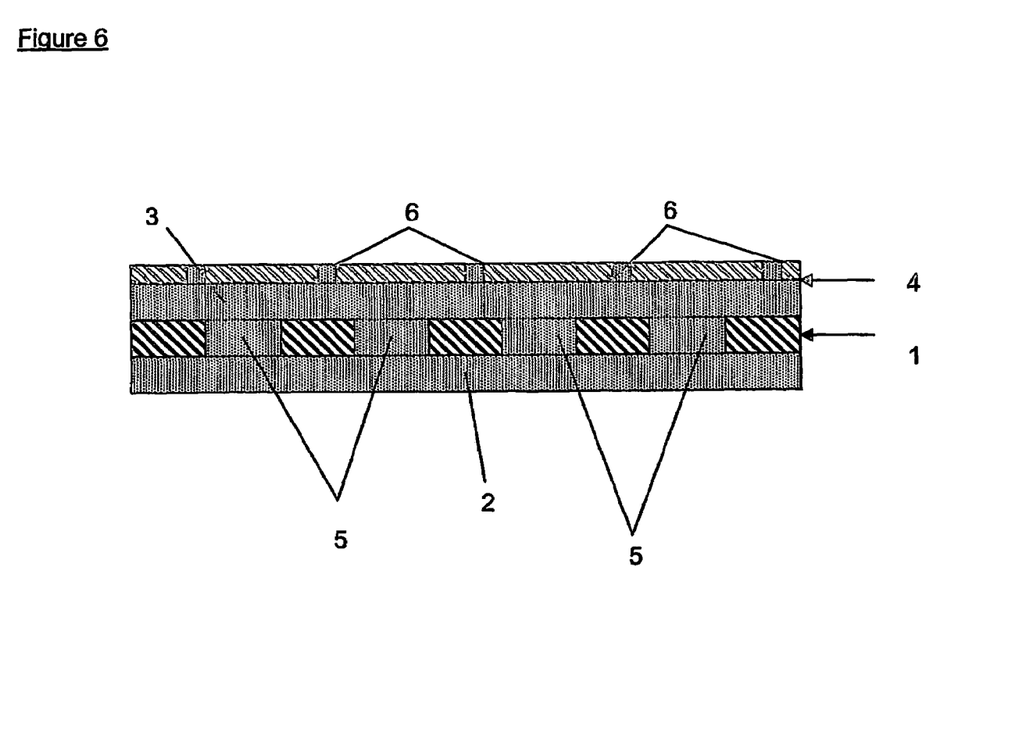
FIG. 6 is a schematic sectional view of a sheet according to the invention.

FIG. 6 shows (schematically and not to scale) the structure of a typical sheet prepared in accordance with the invention. The sheet comprises a core in the form of a film 1 of poly(lactide-co-glycolide) (PLG) which has a regular array of apertures 5. Layers 2,3 of a tissue-reactive formulation are pressed onto both sides of the film 1 such that the tissue-reactive formulation penetrates into, and fills, the apertures. Finally, a non-adhesive layer 4, again of PLG, is applied to one surface of the sheet. The non-adhesive layer 4 is also perforated, the perforations 6 being smaller than the apertures 5 in the core film 1.

The non-adhesive layer 4 may include a chromophore that gives the non-adhesive surface a discernible colour, thereby identifying that surface (and hence indicating which side of the sheet is to be applied to the tissue). Alternatively, the two sides of the sheet may be distinguishable by virtue of a difference in reflectivity of the two surfaces.

EXAMPLE 8

Preparation of Multilayer Sheet Formulation

This Example describes the preparation of a multilayer tissue-adhesive sheet having the structure illustrated schematically in Example 6. The sheet comprises a PLG core, to both sides of which a particulate mixture of NHS-activated PVP-co-PAA is applied. A PLG barrier layer is applied to one side of the sheet.

8.1 Preparation of Poly (DL-lactide-co-glycolide) Core Film

The core film was prepared by casting from a 10 % w/w solution of poly(D,L-lactide-co-glycolide) (PLG) in dichloromethane. The core film was produced by spreading the 10% polymer solution using a 300 µm K Bar (R K Print Coat Instruments Ltd, Royston, UK) on silicon paper. A K Bar is a device for accurately producing films of a specific thickness from a specific concentration solution. After drying, the thickness of the core film was 30 µm.

8.2 Preparation of PLG Barrier Film

The barrier film was produced in an analogous manner to the core film, but using a 24 µm K Bar. After drying, the thickness of the barrier film was 3 µm.

7.3 Preparation of Perforations and Cutting Out of poly(DL-lactide-co-glycolide) Core and Barrier Films The next step was to perforate the core and barrier films. This was carried out using a heated perforating device in the form of a press that had been adapted for the purpose. The press was fitted with a heated plate, the underside of which was formed with a regular array of pyramidal projections.

The perforations were created by applying the heated plate with pressure to the film. This softened the polymer film, which redistributed itself around the small pyramids. For perforating the core film, the heated plate was set to 90° C. and pressed for 10 s. The barrier film was perforated using a temperature of 90° C. for 5 s at a reduced pressing pressure. The perforation size for the core film was 1.3 mm with centre separations of 2.5 mm and the barrier film perforation size was 0.5 mm with centre separations of 2.5 mm. The perforated films were then cut to size, which in this embodiment was a circle of 39.8 mm diameter. Due to redistribution of the film material during perforation, the film thickness increased to 90 µm for the core film and 8-10 µm for the barrier film.

8.4 Preparation of NHS-Activated PVP-co-PAA

NHS-activated PVP-co-PAA was prepared as described in Example 1.

8.5 Preparation of Freeze-Dried Buffered Human Serum Albumin

Freeze-dried buffered human serum albumin (FDBHSA) was prepared by mixing Human Albumin 20% solution with a pH10.5 sodium carbonate/sodium phosphate solution. This solution was lyophilised, leaving powdered human albumin containing sodium carbonate and sodium phosphate evenly distributed throughout.

The pH10.5 sodium carbonate/sodium phosphate solution was prepared by as follows:

31.729 g (0.30 moles) of anhydrous sodium carbonate was weighed into a sterile 250 ml glass bottle. Approximately 200 ml of water for injections was added and the anhydrous sodium carbonate was dissolved by mixing on a roller mixer. Once the sodium carbonate had completely dissolved, the solution was poured into a 1000 ml volumetric flask and made up to 1000 ml with water for injections.

A sodium phosphate solution was made by dissolving 3.560 g (0.03 moles) of sodium phosphate monobasic in approximately 50 ml of water for injections in a glass bottle on a roller mixer. This was poured into a 100 ml volumetric flask and made up to 1 00 ml using water for injections.

The two solutions were mixed in the ratio 470 ml of sodium carbonate solution to 90 ml of sodium phosphate solution. The two solutions were thoroughly mixed and the pH checked using a Mettler Toledo pH meter. The pH of the solution should be in the range of pH 10-11. If the pH is too low, sodium carbonate solution is added, and, if it is too high, sodium phosphate solution is added, until the pH is within the desired range.

Human Albumin 20% solution was mixed 1:1 v/v with pH10.5 sodium carbonate/sodium phosphate in a glass bottle on a roller mixer for around 30 minutes. When fully mixed, the Human albumin/sodium carbonate/phosphate solution was poured into porcelain dishes and frozen in a freezer at approximately −60° C. When the albumin solutions were completely frozen, they were transferred to the drying chamber of an Edwards Supermodulyo freeze-dryer. The chamber was sealed and the vacuum applied. No heat was applied to the shelves and the albumin was left in the freeze-dryer for at least 72 hours. The vacuum achieved was a minimum $10^{-1}$ mbar.

When dry, the material was removed from the freeze-dryer and ground into a fine powder using a pestle and mortar or electric mill.

8.6 Preparation of Mixed NHS-Activated PVP-co-PAA/FDBHSA Powders

The NHS-activated PVP-co-PAA and FDBHSA were ground together in a pestle and mortar until a fine powder was obtained. The ground powder was then mixed on a roller mixer for 30 min prior to use to ensure the two components were fully integrated.

8.7 Preparation of Multilayer Sheet

The final product was assembled in a Specac FT-IR 40 mm die by compression between two pellets. Pieces of silicon paper were used to prevent the finished product sticking to the pellets.

With the first pellet in the die, a silicon paper disc was placed in the cavity and a 150 mg portion of the ground powder was sprinkled onto the silicon paper. The powder was carefully manipulated with a spatula or plunger so that the powder evenly covered the entire base of the die. The 39.8 mm diameter perforated core film was placed on top of the powder layer and firmly pressed so that so that the film was flat and in contact with the powder layer beneath it so that the powder occupied the perforations of the core film. A second 150 mg aliquot of powder was sprinkled onto the perforated PLG core film and again gently levelled.

The perforated barrier layer was placed on a second piece of silicon paper and positioned on top of the second powder layer.

A second die pellet was introduced, and the assembled die placed into the press and compressed to a pressure of 2 tonnes for 30 s. The final product was then removed from between the pellets. The thickness of the final product was in the range 325-425 µm.

The side of the sheet to which the barrier layer is applied had a shiny appearance, and was hence distinguishable from the matt surface of the tissue-reactive side.

Example 9

Application of Sheet to Tissue

The tissue surface is prepared in accordance with conventional surgical technique. The sheet is applied onto (and if necessary) around the tissue surface with moderate pressure to ensure satisfactory contact to the tissue. Following application, the sheet may be hydrated with saline solution.

Example 10

Measurement of Adhesive Strength

A Universal testing machine (UTM, Zwick/Roell BZ2,5) was used to test the adhesive strength of test materials to freshly excised liver or lung tissue. Details of the testing procedure are summarised below.

A small section of tissue (4 cm×4 cm×1 cm (depth)) was prepared and mounted into a purpose-made holder at the base of the test machine. The surface of the tissue was sprayed with water. The test specimen (with sample holder attached to enable subsequent removal) was placed onto the tissue surface with a moderate force to ensure full contact. The material was left on the tissue for 5 minutes and then wholly submerged in water for a further 5 minutes. Whilst holding the tissue in place using a suitable clamp the folded tip of the sample holder was Inserted in the grips of the UTM. The sample was positioned appropriately to ensure that the sample was aligned with the grips. The grip was then moved at 180° from the test sample thereby removing the sample from the tissue. The UTM software (Zwick TestXpert ver 9.0) can be used to calculate the energy of adhesion (mJ) of the test material. Adhesion tests were performed on powder compositions of differing compositions.

Table II shows the data obtained by testing compressed films as a function of composition.

TABLE II

| Test medium Substrate | Tissue reactive material | Crosslinkable material | Ratio of components | Mean energy of adhesion (SD)/mJ (n = 6) |
|---|---|---|---|---|
| Porcine liver | NHS-activated $PVP_{80}$-co-$PAA_{20}$ | Human albumin | 4:1 | 1.3 (0.29) |
| Porcine liver | NHS-activated $PVP_{80}$-co-$PAA_{20}$ | Human albumin | 1:4 | 1.0 (0.43) |
| Porcine liver | NHS-activated $PVP_{80}$-co-$PAA_{20}$ | Human albumin | 1:1 | 1.0 (0.27) |

The results listed in Table II demonstrate the adhesion performance of the co-powder formulations of NHS-activated $PVP_{80}$-co-$PAA_{20}$ and freeze-dried human albumin.

In a further study, Table III illustrates the results of adhesion testing of sheet formulations, (13 mm diameter circular discs) studied as a function of the number of apertures in a PLG film with active co-powders pressed into either side of the PLG film. The powders utilised were NHS-activated $PVP_{80}$co-$PAA_{20}$ and human albumin in a 4:1 ratio.

TABLE III

| Test medium | No of apertures in 13 mm diameter sheet | Mean energy of adhesion (SD)/mJ (n = 6) |
|---|---|---|
| Porcine liver | 0 | 0.39 (0.14) |
| Porcine liver | 10 | 0.75 (0.25) |
| Porcine liver | 20 | 1.14 (0.37) |

The results listed in Table III demonstrate that the energy of adhesion of multi-layered sheets is proportional to the number of apertures in the PLG inner film.

The invention claimed is:

1. A tissue-adhesive formulation comprising a naturally occurring or synthetic polymerisable and/or cross-linkable material in particulate form, the polymerisable and/or cross-linkable material is in admixture with particulate material comprising tissue-reactive functional groups, wherein the polymerisable and/or cross-linkable material is albumin, and wherein the particulate material comprising tissue-reactive functional groups is the reaction product of poly(N-vinyl-2-pyrrolidone-co-acrylic acid) co-polymer and a reactant comprising a tissue-reactive functional group wherein the tissue-reactive functional group is selected from the group consisting of imido ester, p-nitrophenyl carbonate, N-hydroxysuccinimide ester, epoxide, isocyanate, acrylate, vinyl sulfone, orthopyridyl-disulfide, maleimide, aldehyde and iodoacetamide.

2. A formulation according to claim 1, wherein the ratio by weight of polymerisable and/or cross-linkable material to material comprising tissue-reactive functional groups is between 0.1:1 and 10:1.

3. A formulation according to claim 2, wherein the ratio by weight of polymerisable and/or cross-linkable material to material comprising tissue-reactive functional groups is between 0.2:1 and 1:1.

4. A formulation according to claim 1, wherein the tissue-reactive functional groups are N-hydroxysuccinimide esters.

5. A formulation according to claim 1, wherein the poly (N-vinyl-2-pyrrolidone-co-acrylic acid) co-polymer has a molar ratio of acrylic acid-derived units less than 0.60.

6. A formulation according to claim 1, wherein the poly (N-vinyl-2-pyrrolidone-co-acrylic acid) co-polymer has a molar ratio of acrylic acid-derived units between 0.025 and 0.25.

7. A formulation according to claim 1, wherein the poly(N-vinyl-2-pyrrolidone-co-acrylic acid) co-polymer is derivatised with N-hydroxysuccinimide ester to form the material comprising tissue-reactive functional groups.

8. A formulation according to claim 1, wherein the concentration of material comprising tissue-reactive functional groups in the formulation is between 10 and 50% w/w.

9. A formulation according to claim 1, wherein the albumin is porcine, bovine or human albumin.

10. A formulation according to claim 1, wherein the polymerisable and/or cross-linkable material is buffered to a pH greater than 7.

11. A formulation according to claim 1, further comprising one or more components selected from the group of structural polymers, surfactants, and plasticisers.

12. A formulation according to claim 1, wherein the particles that make up the formulation have a median size in the range 5 µm to 500 µm.

13. A formulation according to claim 1, which consists essentially of said naturally occurring or synthetic polymerisable and/or cross-linkable material in particulate form and said particulate material comprising tissue-reactive groups.

14. A sheet having a multilayer structure, said structure consisting of a core of a naturally occurring or synthetic polymeric material, the core being coated on at least one side thereof with a tissue-adhesive formulation according to claim 1.

15. A sheet according to claim 14, wherein the naturally occurring or synthetic polymeric material is selected from the group consisting of polymers or co-polymers based on α-hydroxy acids.

16. A sheet according to claim 14, wherein the naturally occurring or synthetic polymeric material is selected from the group consisting of alginates, polyhydroxyalkanoates, polyamides, polyethylene, propylene glycol, water-soluble glass fibre, starch, cellulose, collagen, pericardium, albumin, polyester, polyurethane, potyeretherketone, polypropylene and polytetrafluoroethylene.

17. A sheet according to claim 14, wherein the core is apertured.

18. A sheet according to claim 17, wherein the sheet has a regular array of apertures, and the apertures are between 50 µm and 2 mm in diameter and adjacent apertures are formed at a centre-to-centre separation of between 100 µm and 5 mm.

19. A sheet according to claim 18, wherein the apertures account for between 5% and 80% of the overall surface area of the core.

20. A sheet according to claim 14, wherein the core has a thickness of 0.005 to 5 mm.

21. A sheet according to claim 14, wherein the tissue-adhesive formulation is applied to the core by mechanically compressing a blend of material containing tissue-reactive functional groups and polymerisable and/or cross-linkable material, both in particulate form, onto one or both sides of the core.

22. A sheet according to claim 14, wherein the core is coated on both sides with the tissue-adhesive formulation.

23. A sheet according to claim 14, wherein one surface of the sheet is coated with a non-adhesive material.

24. A sheet according to claim 23, wherein the non-adhesive material is selected from the group consisting of polyethylene glycols, polylactide and poly(lactide-co-glycolide).

25. A sheet according to claim 24, wherein the non-adhesive coating includes a visibly-absorbing chromophore.

26. A sheet according to claim 25, wherein the visibly-absorbing chromophore is methylthioninium chloride.

27. A sheet according to claim 23, wherein the coating of non-adhesive material is apertured.

28. A method of joining a tissue surface to another tissue, or of sealing a tissue surface, which method comprises applying to the tissue surface a formulation according to claim 1.

29. A method as claimed in claim 28, wherein the formulation is present on a sheet having a multilayer structure consisting of a core formed of a naturally occurring or synthetic polymeric material, with the formulation being present as a coating on at least one side of the core.

30. A method as claimed in claim 28, wherein the method is carried out to enhance wound healing, promote wound closure, provide reinforcement in hernia repair procedures, seal joint tubular structures, seal resected tissue sections, seal air leaks in lung tissue, promote haemostasis, or prevent post-surgical adhesions.

31. A method of joining a tissue surface to another tissue, or of sealing a tissue surface, which method comprises applying to the tissue surface a composition according to claim 14.

32. A method as claimed in claim 31, wherein the method is carried out to enhance wound healing, promote wound closure, provide reinforcement in hernia repair procedures, seal joint tubular structures, seal resected tissue sections, seal air leaks in lung tissue, promote haemostasis, or prevent post-surgical adhesions.

* * * * *

UNITED STATES PATENT AND TRADEMARK OFFICE
CERTIFICATE OF CORRECTION

| | | |
|---|---|---|
| PATENT NO. | : 7,727,547 B2 | Page 1 of 1 |
| APPLICATION NO. | : 10/552095 | |
| DATED | : June 1, 2010 | |
| INVENTOR(S) | : Fortune et al. | |

It is certified that error appears in the above-identified patent and that said Letters Patent is hereby corrected as shown below:

On the cover page, on the first line beneath item (30) Foreign Applications Priority Data, delete "April 4, 2000" and insert --April 4, 2003-- in its place.

Signed and Sealed this

Twenty-sixth Day of October, 2010

David J. Kappos
*Director of the United States Patent and Trademark Office*